US012778454B2

(12) United States Patent
Du et al.

(10) Patent No.: US 12,778,454 B2
(45) Date of Patent: Nov. 3, 2026

(54) SAFE RIDING DETECTION METHOD AND WEARABLE DEVICE

(71) Applicant: Robert Bosch GmbH, Stuttgart (DE)

(72) Inventors: Bin Du, Shanghai (CN); Xu Han, Shanghai (CN)

(73) Assignee: Robert Bosch GmbH, Stuttgart (DE)

( * ) Notice: Subject to any disclaimer, the term of this patent is extended or adjusted under 35 U.S.C. 154(b) by 396 days.

(21) Appl. No.: 18/513,582

(22) Filed: Nov. 19, 2023

(65) Prior Publication Data

US 2024/0164664 A1 May 23, 2024

(30) Foreign Application Priority Data

Nov. 23, 2022 (CN) ......................... 202211472517.1

(51) Int. Cl.

*A61B 5/11* (2006.01)
*A61B 5/00* (2006.01)
*G01C 9/02* (2006.01)

(52) U.S. Cl.

CPC ........... *A61B 5/1117* (2013.01); *A61B 5/1114* (2013.01); *A61B 5/1121* (2013.01); *A61B 5/6803* (2013.01); *A61B 5/681* (2013.01); *A61B 5/7282* (2013.01); *G01C 9/02* (2013.01); *A61B 2503/10* (2013.01); *A61B 2560/0257* (2013.01)

(58) Field of Classification Search

CPC ... A61B 5/1117; A61B 5/1114; A61B 5/1121; A61B 5/6803; A61B 5/681; A61B 5/7282; A61B 2503/10; A61B 2560/0257; G01C 9/02

See application file for complete search history.

(56) References Cited

U.S. PATENT DOCUMENTS

| | | | | |
|---|---|---|---|---|
| 5,778,879 | A * | 7/1998 | Ota | A61B 5/022 600/503 |
| 10,806,375 | B2 * | 10/2020 | Ortega | A61B 5/02055 |
| 10,884,504 | B2 * | 1/2021 | Kim | G06F 3/017 |
| 10,905,374 | B2 * | 2/2021 | Gupta | A61B 5/1121 |
| 2003/0034622 | A1 * | 2/2003 | van Ardenne | B62K 21/00 280/87.05 |
| 2007/0145708 | A1 * | 6/2007 | Davioni | B62M 1/12 280/233 |
| 2018/0317811 | A1 * | 11/2018 | Lee | A61B 5/1114 |
| 2019/0001776 | A1 * | 1/2019 | Murakami | B60G 17/044 |
| 2020/0258365 | A1 * | 8/2020 | Ten Kate | G08B 21/0446 |

* cited by examiner

*Primary Examiner* — Thomas D Alunkal

(74) *Attorney, Agent, or Firm* — Maginot, Moore & Beck LLP

(57) ABSTRACT

A safe riding detection method includes (i) utilizing a first wearable device to detect a first height and first posture of a first body part used for wearing the first wearable device, (ii) utilizing a second wearable device to detect a second height and second posture of a second body part used for wearing the second wearable device, and (iii) determining whether a riding anomaly or fall has occurred based on the first height, first posture, second height, and second posture. A wearable device and a computer storage medium is also disclosed.

16 Claims, 2 Drawing Sheets

SAFE RIDING DETECTION METHOD AND WEARABLE DEVICE

This application claims priority under 35 U.S.C. § 119 to patent application no. CN 2022 1147 2517.1, filed on Nov. 23, 2022 in China, the disclosure of which is incorporated herein by reference in its entirety.

The present disclosure relates to a safe riding detection solution, and more specifically, to a safe riding detection method, a wearable device, and a computer storage medium.

BACKGROUND

Vehicles such as bicycles, electric bicycles, and motorcycles have become commonly used means of transportation in people's daily lives due to their small size and agile maneuverability. However, due to the lack of safety devices on bicycles, electric bicycles, and motorcycles, it is common to see cyclists not wearing helmets or wearing them incorrectly, which seriously endangers traffic safety and people's lives and property. Furthermore, family members or guardians would like to be kept informed as to whether the cyclist is safe while riding, such as whether a fall has occurred or if a helmet is not being worn, etc.

However, wearable devices available in the market, such as smart watches and helmets, are unable to accurately detect helmet usage in real time, and their accuracy in detecting falls or injuries during riding is also relatively low.

SUMMARY

According to an aspect of the present disclosure, a safe riding detection method is provided, wherein the method includes utilizing a first wearable device to detect a first height and first posture of a first body part used for wearing the first wearable device; utilizing a second wearable device to detect a second height and second posture of a second body part used for wearing the second wearable device; and determining whether a riding anomaly or fall has occurred based on the first height, first posture, second height, and second posture.

As a supplement or alternative to the above-mentioned solution, in the method described above, the first wearable device is a helmet, the first body part is the head, the second wearable device is a smart watch, and the second body part is an arm or a wrist.

As a supplement or alternative to the above-mentioned solution, in the method described above, the riding anomalies include holding onto the bike handlebars with one hand for an extended period or letting go of both hands while riding; frequently looking left and right while riding; keeping the head turned away from the direction of travel for an extended period while riding; and not wearing the helmet correctly when riding.

As a supplement or alternative to the above-mentioned solution, in the method described above, utilizing a first wearable device to detect the first height and first posture of the first body part used for wearing the first wearable device includes utilizing an air pressure sensor in the helmet to detect an air pressure P1 at the height of the head; and utilizing a posture measurement device in the helmet to detect a head posture Q1.

As a supplement or alternative to the above-mentioned solution, in the method described above, utilizing a second wearable device to detect the second height and second posture of the second body part used for wearing the second wearable device includes utilizing an air pressure sensor in the smart watch to detect an air pressure P2 at the height of the wrist; and utilizing a posture measurement device in the smart watch to detect a wrist posture Q2.

As a supplement or alternative to the above-mentioned solution, in the method described above, determining whether a riding anomaly or fall has occurred based on the first height, first posture, second height, and second posture includes calculating the height difference ΔH between air pressure P1 at the height of the head and air pressure P2 at the height of the wrist; utilizing the posture measurement device in the helmet to detect a pitch angle θ1 and a roll angle θ2 of the helmet; and determining whether the helmet is correctly worn based on the height difference ΔH, pitch angle θ1, and roll angle θ2.

As a supplement or alternative to the above-mentioned solution, in the method described above, the head posture Q1 and the wrist posture Q2 are represented using quaternions, and determining whether a riding anomaly or fall has occurred based on the first height, first posture, second height, and second posture further includes determining that a riding anomaly or fall has occurred when the height difference ΔH is less than the first threshold, and the head posture Q1 and the wrist posture Q2 are outside a predefined range.

As a supplement or alternative to the above-mentioned solution, in the method described above, determining whether a riding anomaly or fall has occurred based on the first height, first posture, second height, and second posture further includes calculating a relative wrist-to-head posture ΔQ based on the head posture Q1 and the wrist posture Q2; and determining whether the hands have left the handlebars based on the relative wrist-to-head posture ΔQ and the height difference ΔH between the head and wrist.

According to another aspect of the present disclosure, a wearable device is provided, wherein comprises: a receiving unit that is used to receive the first height and first posture of the first body part used for wearing another wearable device from said other wearable device; a detection unit that is used to detect the second height and second posture of the second body part used for wearing the wearable device; and a determination unit that is used to determine whether a riding anomaly or fall has occurred based on the first height, first posture, second height, and second posture.

As a supplement or alternative to the above-mentioned solution, in the device described above, the wearable device is a smart watch, the other wearable device is a helmet, the first body part is the head, and the second body part is an arm or a wrist.

As a supplement or alternative to the above-mentioned solution, in the device described above, the detection unit comprises: an air pressure sensor used for detecting an air pressure P2 at the height of the wrist; and a posture measurement device used for detecting a wrist posture Q2.

As a supplement or alternative to the above-mentioned solution, in the device described above, the other wearable device comprises an air pressure sensor for detecting an air pressure P1 at the height of the head, and a posture measurement device for detecting a head posture Q1, and the determination unit is configured for calculating the height difference ΔH between air pressure P1 at the height of the head and air pressure P2 at the height of the wrist; utilizing the posture measurement device in the helmet to detect a pitch angle θ1 and a roll angle θ2 of the helmet; and determining whether the helmet is correctly worn based on the height difference ΔH, pitch angle θ1, and roll angle θ2.

As a supplement or alternative to the above-mentioned solution, in the method described above, the head posture Q1 and the wrist posture Q2 are represented using quaternions, and the determination unit is further configured for determining that a riding anomaly or fall has occurred when the height difference ΔH is less than the first threshold, and the head posture Q1 and the wrist posture Q2 are outside a predefined range.

As a supplement or alternative to the above-mentioned solution, in the device described above, the determination unit is further configured for calculating the relative wrist-to-head posture ΔQ based on the head posture Q1 and the wrist posture Q2; and determining whether the hands have left the handlebars based on the relative wrist-to-head posture ΔQ and the height difference ΔH between the head and wrist.

According to yet another aspect of the present disclosure, a computer storage medium is provided, including instructions that, when executed, perform the method as described above.

In the examples of the present disclosure, the safe riding detection method utilizes both the first wearable device and the second wearable device to detect the first height and first posture of the first body part, as well as the second height and second posture of the second body part, respectively; and determines whether a riding anomaly or fall has occurred based on the first height, first posture, second height, and second posture. In this way, the first wearable device and the second wearable device work in concert to detect riding anomalies, such as improper helmet usage, or incidents of falling and getting injured. This detection method/solution is more precise compared to existing detection methods and is advantageous in providing a more comprehensive riding service, such as promptly notifying a family member or guardian in the event of a cyclist falling or experiencing a riding anomaly.

BRIEF DESCRIPTION OF DRAWINGS

The foregoing and other objectives and advantages of the present disclosure will become more fully apparent from the following detailed description taken in conjunction with the accompanying drawings, in which identical or similar elements are denoted by the same reference numerals.

DETAILED DESCRIPTION

In the following text, a safe riding detection solution according to various exemplary examples of the present disclosure will be described in detail with reference to the accompanying drawings.

Figure 1:
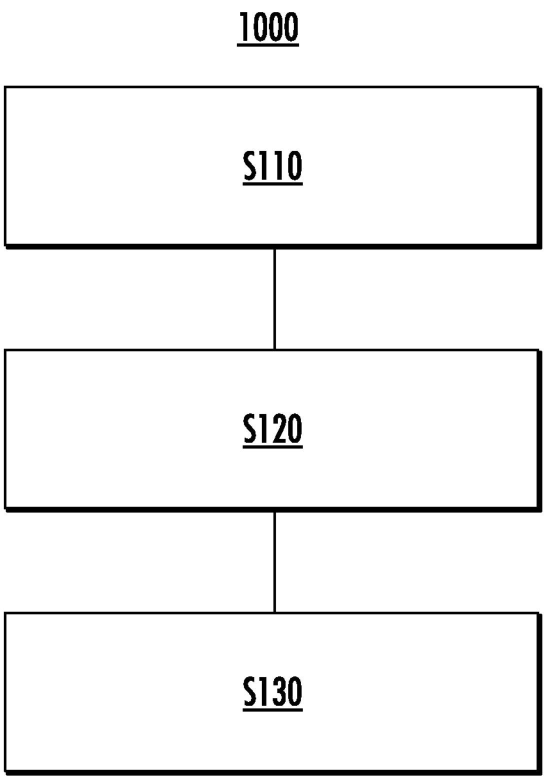
FIG. 1 shows a flow diagram of a safe riding detection method according to an example of the present disclosure.

FIG. 1 shows a schematic diagram of a safe riding detection method 1000 according to an example of the present disclosure. As shown in FIG. 1, the safe riding detection method 1000 includes

- a Step S110, utilizing a first wearable device to detect a first height and first posture of a first body part used for wearing the first wearable device;
- a Step S120, utilizing a second wearable device to detect a second height and second posture of a second body part used for wearing the second wearable device; and
- a Step S130, determining whether a riding anomaly or fall has occurred based on the first height, first posture, second height, and second posture.

In the context of the present disclosure, the term "wearable device" may also be referred to as a wearable gadget or a wearable, which means a portable device that can be worn directly on the body or integrated into a piece of clothing or an accessory of a user. In one or more examples, the wearable device may come in various product forms, including wrist-supported products such as a watch and wrist band, foot-supported products such as shoes, socks, or other leg-worn products, head-supported products such as glasses, helmet, headband, as well as smart clothing, backpack, cane, accessory, and the like.

In an example, the first wearable device is a helmet, the first body part used for wearing the first wearable device is the head, the second wearable device is a smart watch, and the second body part used for wearing the second wearable device is an arm or a wrist.

In the context of the present disclosure, the term "riding anomaly" refers to an abnormal riding state, such as holding onto the bike handlebars with one hand for an extended period or letting go of both hands while riding; frequently looking left and right while riding; keeping the head turned away from the direction of travel for an extended period while riding; and not wearing the helmet correctly when riding (e.g., wearing the helmet on the shoulder or hanging it at the back of the head).

In one or more examples of the present disclosure, posture includes posture of the head and posture of the arms. A head posture, for example, may include movements like tilting the head left or right, turning the head left or right, nodding up and down, and so on; arm/wrist posture may include such actions as gripping the handlebar(s), letting go of the handlebar(s), raising the arm(s), lowering the arm(s), and so on. The posture of a cyclist is determined based on the head and arm/wrist posture, as well as the height difference between the head and the arm/wrist.

In Step S110, the first wearable device is used to detect the first height and first posture of the first body part used for wearing the first wearable device. For example, Step S110 includes utilizing an air pressure sensor in a helmet to detect an air pressure P1 at the height of the head; and utilizing a posture measurement device in the helmet to detect a head posture Q1.

In the context of the present disclosure, the term "posture measurement device" includes various devices capable of measuring posture, including but not limited to inertial measurement units (IMU), G-sensors, gyroscopes, magnetic sensors, or combinations thereof.

In Step S120, the second wearable device is used to detect the second height and second posture of the second body part used for wearing the second wearable device. For example, Step S120 includes utilizing an air pressure sensor in a smart watch to detect an air pressure P2 at the height of the wrist; and utilizing a posture measurement device in the smart watch to detect a wrist posture Q2.

Combining both the air pressure sensor and the posture measurement device enables a more accurate assessment of the riding posture, resulting in significantly lower rates of misjudgment compared to existing solutions. After obtaining the first height, first posture, second height, and second posture, in Step S130, it is possible to determine whether a riding anomaly or fall has occurred based on the height and posture information obtained.

In an example, Step S130 includes calculating the height difference ΔH between air pressure P1 at the height of the head and air pressure P2 at the height of the wrist; utilizing the posture measurement device in the helmet to detect a pitch angle θ1 and a roll angle θ2 of the helmet; and determining whether the helmet is correctly worn based on the height difference ΔH, pitch angle θ1, and roll angle θ2.

Specifically, the height difference ΔH between the head and the wrist may be calculated using the following formula:

$$\Delta H = \frac{\Delta P}{\rho g},$$

where ΔP=P2−P1 represents the difference between the air pressure P2 at the height of the wrist and the air pressure P1 at the height of the head, with P2 and P1 measured in units of Pa.

Figure 3:
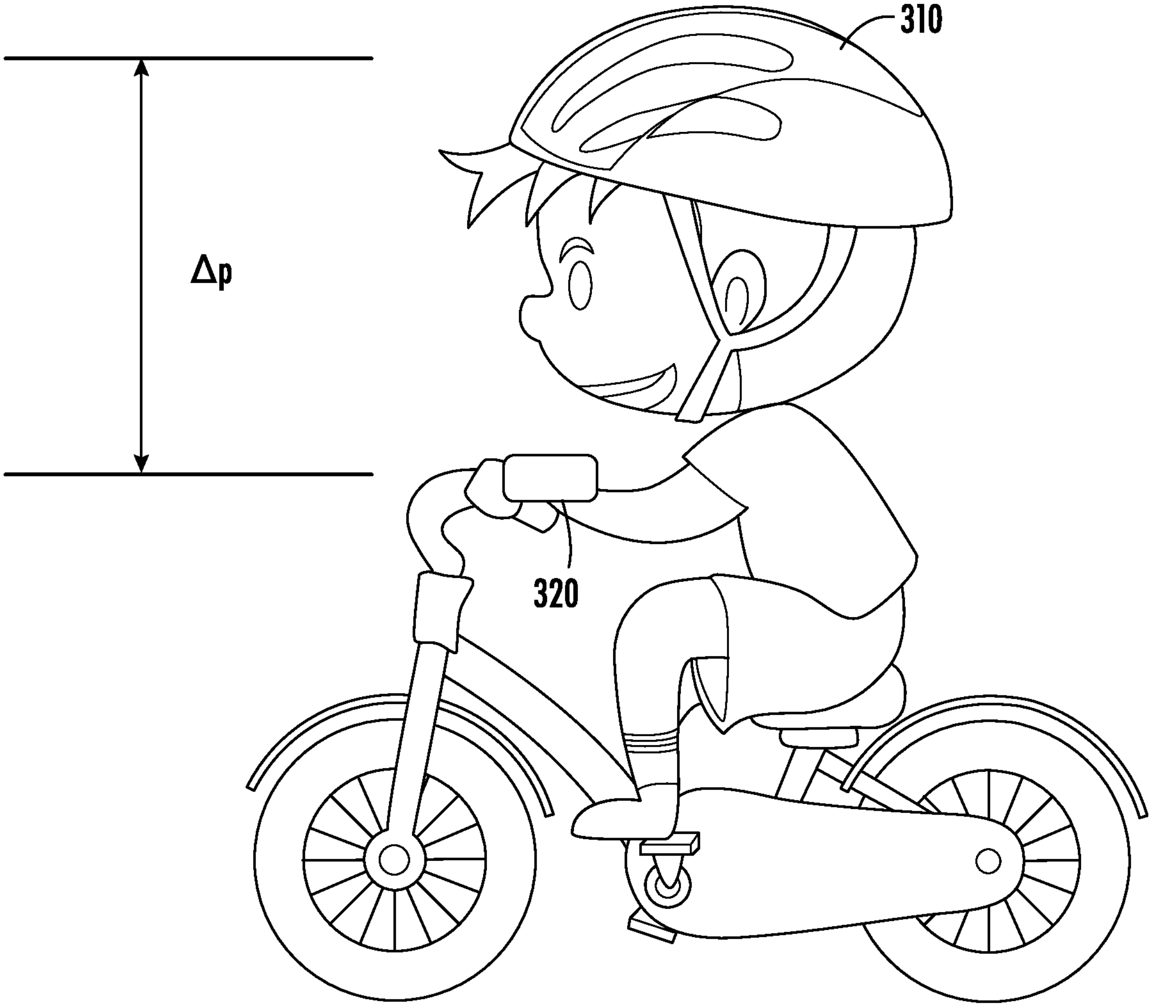
FIG. 3 shows a schematic diagram of detecting the height difference between the first wearable device and the second wearable device according to an example of the present disclosure.

FIG. 3 shows a schematic diagram of detecting the height difference between the first wearable device 310 and the second wearable device 320 according to an example of the present disclosure. By detecting the air pressure difference ΔP between a sensor in the first wearable device 310 (the helmet) and a sensor in the second wearable device 320 (the smart watch), the height difference ΔH between the head and wrist may be further determined.

In the formula for calculating the height difference ΔH between the head and the wrist, ρ represents air density, measured in units of $kg/m^3$, and g represents gravitational acceleration, measured in units of N/kg. Both ρ and g are constants, so it may be understood that the difference in measured air pressure values at different positions may be used to derive the height difference ΔH. The height difference ΔH should be maintained within a reasonable range in a normal riding state (e.g., helmet on top of the head and arms on the handlebars). If the height difference ΔH exceeds the normal range, it may be considered an anomaly.

The posture measurement device may be used to detect the pitch angle θ1 and roll angle θ2 of the helmet, whereby the pitch angle θ1 and roll angle θ2 are used to track the orientation of the head (assuming the helmet is correctly worn). During the riding process, the pitch angle and roll angle of the head should stay within a certain range—if the pitch angle θ1 and roll angle θ2 of the helmet exceed the normal range, it may be considered an anomaly.

In an example, determining whether a helmet is correctly worn according to the height difference ΔH, the pitch angle θ1, and the roll angle θ2 includes: the helmet is determined to be correctly worn only when the height difference ΔH, pitch angle θ1, and roll angle θ2 are all within the normal range. Conversely, if any of the height difference ΔH, pitch angle θ1, or roll angle θ2 exceeds a reasonable/normal range, it is determined that the helmet is not correctly worn.

In one or more examples, the head posture Q1 and the wrist posture Q2 are represented using quaternions. The term "quaternion" refers to a simple hypercomplex number. A complex number is composed of a real number and an imaginary unit i, where $i^2=-1$. Similarly, a quaternion is composed of a real number and three imaginary units i, j, and k, and they follow the following relationship: $i^2=j^2=k^2=-1$. Each quaternion is a linear combination of 1, i, j, and k, and can be generally represented as a+bi+cj+dk, where a, b, c, and d are real numbers. The geometric interpretation of i, j, and k can be understood as rotations, wherein, i represents a rotation about the Z-axis intersecting the Y-axis plane with the Z-axis rotating towards the positive Y-axis; j represents a rotation about the X-axis intersecting the Z-axis plane with the X-axis rotating towards the positive Z-axis; k represents a rotation about the Y-axis intersecting the X-axis plane with the Y-axis rotating towards the positive X-axis; and −i, −j, and −k represent the reverse rotations of i, j, and k, respectively. In this example, Step S130 includes determining that a riding anomaly or fall has occurred when the height difference ΔH is less than the first threshold (for example, when height difference ΔH is very small or even negative), and the head posture Q1 and the wrist posture Q2 are outside a predefined range (for example, when their values are abnormal).

In an example, Step S130 may further include calculating a relative wrist-to-head posture ΔQ based on the head posture Q1 and the wrist posture Q2; and determining whether the hands have left the handlebars based on the relative wrist-to-head posture ΔQ and the height difference ΔH between the head and wrist. The head posture Q1 may be represented by a quaternion, which is calculated using a posture measurement device (such as an inertial measurement unit (IMU)) inside the helmet. The wrist posture Q2 of the wrist may also be represented by a quaternion, which may be calculated using a posture measurement device in the smart watch. The relative wrist-to-head posture ΔQ is the difference between the head posture Q1 and the wrist posture Q2.

Although not shown in FIG. 1, in an example, the first wearable device and the second wearable device may be connected via wireless technology such as Bluetooth (e.g., BLE). In this way, the detection data from the first wearable device and the second wearable device may be transmitted via Bluetooth. For example, the height data and posture data detected by a sensor in a smart helmet may be transmitted to a smart watch via Bluetooth. Based on wrist posture, head posture, and the height difference between the wrist and the head, a smart watch or other third-party device is capable of detecting whether a helmet is worn during a ride and whether the cyclist has fallen or been injured. Moreover, generally speaking, a smart watch is a device that is worn regularly, while a helmet is worn only during riding. Therefore, based on the configuration of a smart watch (such as GPS, 4G wireless network, etc.), it may be easier to consolidate and send information about an anomaly to the mobile phone of a guardian or family member of the cyclist.

In other examples, the information from the smart watch and helmet (such as height data and posture data) may also be consolidated to a vehicle terminal or the helmet itself, both of which are capable of detecting whether a cyclist has fallen or been injured and then sending this anomaly information to the mobile phone of a family member or guardian of the cyclist.

Furthermore, it will be readily understood by those skilled in the art that the safe riding detection method 1000 provided in one or more examples of the present disclosure may be implemented through a computer program. For example, this computer program is included in a computer program product that is capable of implementing the safe riding detection method 1000 in one or more examples of the present disclosure when executed by a processor. Similarly, for example, when a computer storage medium (e.g., a USB flash drive) with which the computer program is stored is connected to a computer, running the computer program will execute the safe riding detection method 1000 in one or more examples of the present disclosure.

Figure 2:
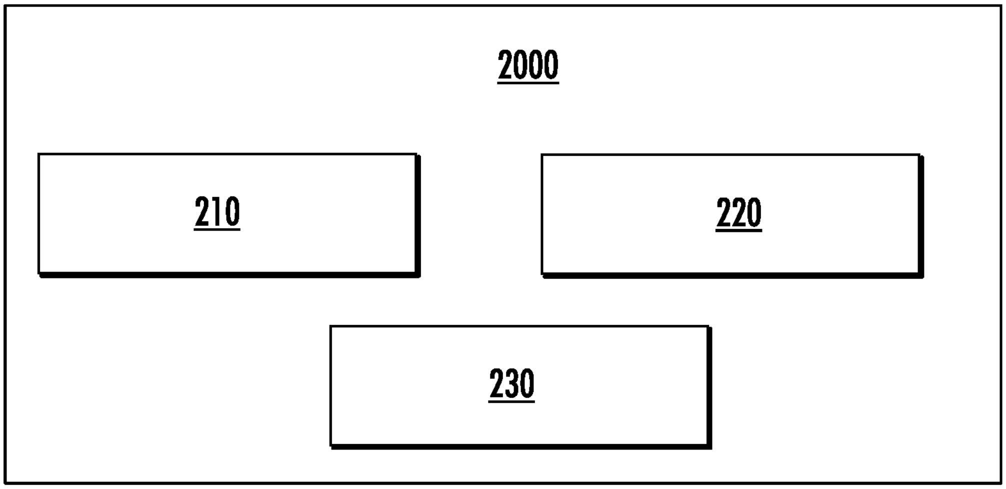
FIG. 2 shows a structural schematic diagram of a wearable device according to an example of the present disclosure.

Refer to FIG. 2, which shows a structural schematic diagram of a wearable device 2000 according to an example of the present disclosure. As shown in FIG. 2, the wearable device 2000 comprises: a receiving unit 210, a detection unit 220, and a determination unit 230. Among these, the receiving unit 210 is used to receive the first height and first posture of the first body part used for wearing another wearable device from said other wearable device; the detection unit 220 is used to detect the second height and second posture of the second body part used for wearing the wearable device; and the determination unit 230 is used to determine whether a riding anomaly or fall has occurred based on the first height, first posture, second height, and second posture.

In the context of the present disclosure, the term "wearable device" may also be referred to as a wearable gadget or a wearable, which means a portable device that can be worn directly on the body or integrated into a piece of clothing or an accessory of a user. In one or more examples, the wearable device may come in various product forms, including wrist-supported products such as a watch and wrist band, foot-supported products such as shoes, socks, or other leg-worn products, head-supported products such as glasses, helmet, headband, as well as smart clothing, backpack, cane, accessory, and the like.

In an example, the wearable device is a smart watch, the other wearable device is a helmet, the first body part is the head, and the second body part is an arm or a wrist.

In the context of the present disclosure, the term "riding anomaly" refers to an abnormal riding state, such as holding onto the bike handlebars with one hand for an extended period or letting go of both hands while riding; frequently looking left and right while riding; keeping the head turned away from the direction of travel for an extended period while riding; and not wearing the helmet correctly when riding (e.g., wearing the helmet on the shoulder or hanging it at the back of the head).

In one or more examples of the present disclosure, posture includes the posture of the head and the posture of the arms. A head posture, for example, may include movements like tilting the head left or right, turning the head left or right, nodding up and down, and so on; arm/wrist posture may include such actions as gripping the handlebar(s), letting go of the handlebar(s), raising the arm(s), lowering the arm(s), and so on. The posture of a cyclist is determined based on the head and arm/wrist posture, as well as the height difference between the head and the arm/wrist.

In an example, the detection unit 220 includes an air pressure sensor used for detecting an air pressure P2 at the height of the wrist; and a posture measurement device used for detecting a wrist posture Q2.

In the context of the present disclosure, the term "posture measurement device" includes various devices capable of measuring posture, including but not limited to inertial measurement units (IMU), G-sensors, gyroscopes, magnetic sensors, or combinations thereof.

In an example, the other wearable device (such as helmet) includes an air pressure sensor for detecting an air pressure P1 at the height of the head, and a posture measurement device for detecting a head posture Q1. Combining both the air pressure sensor and the posture measurement device, the determination unit 230 is capable of providing a more accurate assessment of the riding posture, resulting in significantly lower rates of misjudgment compared to existing solutions.

In an example, the determination unit 230 is configured for calculating the height difference ΔH between air pressure P1 at the height of the head and air pressure P2 at the height of the wrist; utilizing the posture measurement device in the helmet to detect a pitch angle θ1 and a roll angle θ2 of the helmet; and determining whether the helmet is correctly worn based on the height difference ΔH, pitch angle θ1, and roll angle θ2.

Specifically, the height difference ΔH between the head and the wrist may be calculated using the following formula:

$$\Delta H = \frac{\Delta P}{\rho g},$$

where ΔP=P2−P1 represents the difference between the air pressure P2 at the height of the wrist and the air pressure P1 at the height of the head, with P2 and P1 measured in units of Pa. ρ represents air density, measured in units of $kg/m^3$, and g represents gravitational acceleration, measured in units of N/kg. Both ρ and g are constants, so it may be understood that the difference in measured air pressure values at different positions may be used to derive the height difference ΔH. The height difference ΔH should be maintained within a reasonable range in a normal riding state (e.g., helmet on top of the head and arms on the handlebars). If the height difference ΔH exceeds the normal range, it may be considered an anomaly.

The posture measurement device may be used to detect the pitch angle θ1 and roll angle θ2 of the helmet, whereby the pitch angle θ1 and roll angle θ2 are used to track the orientation of the head (assuming the helmet is correctly worn). During the riding process, the pitch angle and roll angle of the head should stay within a certain range—if the pitch angle θ1 and roll angle θ2 of the helmet exceed the normal range, it may be considered an anomaly.

In an example, the determination unit 230 is configured such that the helmet is determined to be correctly worn only when the height difference ΔH, pitch angle θ1, and roll angle θ2 are all within the normal range. Conversely, if any of the height difference ΔH, pitch angle θ1, or roll angle θ2 exceeds a reasonable/normal range, it is determined that the helmet is not correctly worn.

In one or more examples, the head posture Q1 and the wrist posture Q2 are represented using quaternions. The term "quaternion" refers to a simple hypercomplex number. A complex number is composed of a real number and an imaginary unit i, where $i^2=-1$. Similarly, a quaternion is composed of a real number and three imaginary units i, j, and k, and they follow the following relationship: $i^2=j^2=k^2=-1$. Each quaternion is a linear combination of 1, i, j, and k, and can be generally represented as a+bi+cj+dk, where a, b, c, and d are real numbers. The geometric interpretation of i, j, and k can be understood as rotations, wherein, i represents a rotation about the Z-axis intersecting the Y-axis plane with the Z-axis rotating towards the positive Y-axis; j represents a rotation about the X-axis intersecting the Z-axis plane with the X-axis rotating towards the positive Z-axis; k represents a rotation about the Y-axis intersecting the X-axis plane with the Y-axis rotating towards the positive X-axis; and −i, −j, and −k represent the reverse rotations of i, j, and k, respectively.

In this example, the determination unit 230 is configured for determining that a riding anomaly or fall has occurred when the height difference ΔH is less than the first threshold (for example, when height difference ΔH is very small or even negative), and the head posture Q1 and the wrist posture Q2 are outside a predefined range (for example, when their values are abnormal).

In one or more examples, the determination unit 230 may be further configured for calculating a relative wrist-to-head posture ΔQ based on the head posture Q1 and the wrist posture Q2; and determining whether the hands have left the handlebars based on the relative wrist-to-head posture ΔQ and the height difference ΔH between the head and wrist. Furthermore, in one example, the determination unit 230 is configured for determining that a riding anomaly has occurred when the hands leave the handlebars, and that there is no anomaly when the hands remain on the handlebars.

In summary, in the examples of the present disclosure, the safe riding detection method utilizes both the first wearable device and the second wearable device to detect the first height and first posture of the first body part, as well as the second height and second posture of the second body part, respectively; and determines whether a riding anomaly or fall has occurred based on the first height, first posture, second height, and second posture. In this way, the first wearable device and the second wearable device work in concert to detect riding anomalies, such as improper helmet usage, or incidents of falling and getting injured. This detection method/solution is more precise compared to existing detection methods and is advantageous in providing a more comprehensive riding service, such as promptly notifying a family member or guardian in the event of a cyclist falling or experiencing a riding anomaly.

The examples above mainly illustrate a helmet detection solution provided in the examples of the present disclosure. Although only some of the embodiments of the present disclosure have been described, it should be understood by those with ordinary skill in the art that the present disclosure may be implemented in many other forms without departing from its spirit and scope. Therefore, the examples and embodiments presented are illustrative rather than limiting, and without departing from the spirit and scope defined by the claims, the present disclosure may encompass various modifications and replacements.

What is claimed is:

1. A safe riding detection method, comprising:

detecting, with a first wearable device, a first height and a first posture of a first body part used for wearing the first wearable device;

detecting, with a second wearable device, a second height and a second posture of a second body part used for wearing the second wearable device; and determining whether a riding anomaly or fall has occurred based on the first height, the first posture, the second height, and the second posture by evaluating a predefined relationship between the first height, the first posture, the second height, and the second posture, the predefined relationship representing a relative positional arrangement between the first and second body parts.

2. The method as claimed in claim 1, wherein:

the first wearable device is a helmet, the first body part is a head, the second wearable device is a smart watch, and the second body part is an arm or a wrist.

3. The method as claimed in claim 1, wherein the riding anomalies include:

holding onto bike handlebars with one hand for an extended period or letting go of both hands while riding;

frequently looking left and right while riding;

keeping a head turned away from a direction of travel for an extended period while riding; and not wearing a helmet correctly when riding.

4. The method as claimed in claim 2, wherein detecting the first height and the first posture of the first body part used for wearing the first wearable device includes:

detecting, with a first air pressure sensor in the helmet, a first air pressure at a height of the head; and detecting, with a first posture measurement device in the helmet, a head posture.

5. The method as claimed in claim 4, wherein detecting the second height and the second posture of the second body part used for wearing the second wearable device includes:

detecting, with a second air pressure sensor in the smart watch, a second air pressure at a height of the wrist; and detecting, with a second posture measurement device in the smart watch, a wrist posture.

6. The method as claimed in claim 5, wherein;

the detecting of the head posture includes detecting a pitch angle and a roll angle of the helmet using the first posture measurement device; and the determining whether a riding anomaly or fall has occurred includes:

calculating a height difference between the first height and the second height based on the first air pressure at the height of the head and the second air pressure at the height of the wrist; and determining whether the helmet is correctly worn based on the height difference, the pitch angle, and the roll angle.

7. The method as claimed in claim 5, wherein:

the head posture and the wrist posture are represented using quaternions, and the determining whether a riding anomaly or fall has occurred further includes:

calculating a height difference between the first height and the second height based on the first air pressure at the height of the head and the second air pressure at the height of the wrist; and determining that a riding anomaly or fall has occurred when the height difference is less than a first threshold, and the head posture and the wrist posture are outside a predefined range.

8. The method as claimed in claim 5, wherein:

the head posture and the wrist posture are represented using quaternions, and the determining whether a riding anomaly or fall has occurred further includes:

calculating a height difference between the first height and the second height based on the first air pressure at the height of the head and the second air pressure at the height of the wrist;

calculating a relative wrist-to-head posture based on the head posture and the wrist posture; and determining whether hands have left handlebars based on the relative wrist-to-head posture and the height difference between the head and the wrist.

9. A wearable device, comprising:

a wireless receiver configured to receive a first height of a first body part and a first posture of the first body part used for wearing another wearable device from said other wearable device;

a detection unit configured to detect a second height of a second body part and a second posture of the second body part used for wearing the wearable device; and a processor configured to determine whether a riding anomaly or fall has occurred based on the first height, the first posture, the second height, and the second posture by evaluating a predefined relationship between the first height, the first posture, the second height, and the second posture, the predefined relationship representing a relative positional arrangement between the first and second body parts.

10. The device as claimed in claim 9, wherein:
the wearable device is a smart watch,
the other wearable device is a helmet,
the first body part is a head, and
the second body part is an arm or a wrist.

11. The device as claimed in claim 10, wherein the detection unit comprises:
an air pressure sensor configured to detect a first air pressure at a height of the wrist; and
a first posture measurement device configured to detect a wrist posture.

12. The device as claimed in claim 11, wherein:
the wireless receiver is configured to receive (i) a second air pressure detected by the other wearable device at a height of the head, and (ii) a head posture detected by the other wearable device, which includes a pitch angle and a roll angle of the helmet, and
the processor is configured to (i) calculate a height difference between the height of the head and the height of the wrist based on the first air pressure and the second air pressure, and (ii) determine whether the helmet is correctly worn based on the height difference, the pitch angle, and the roll angle.

13. The device as claimed in claim 11, wherein:
the wireless receiver is configured to receive (i) a second air pressure detected by the other wearable device at a height of the head, and (ii) a head posture detected by the other wearable device, which includes a pitch angle and a roll angle of the helmet,
the head posture and the wrist posture are represented using quaternions, and the processor is further configured to (i) calculate a height difference between the height of the head and the height of the wrist based on the first air pressure and the second air pressure and (ii) determine that a riding anomaly or fall has occurred when the height difference is less than a first threshold, and the head posture and the wrist posture are outside a predefined range.

14. The device as claimed in claim 11, wherein:
the wireless receiver is configured to receive (i) a second air pressure detected by the other wearable device at a height of the head, and (ii) a head posture detected by the other wearable device, which includes a pitch angle and a roll angle of the helmet,
the head posture and the wrist posture are represented using quaternions, and
the processor is further configured to (i) calculate a height difference between the height of the head and the height of the wrist based on the first air pressure and the second air pressure, (ii) calculate a relative wrist-to-head posture based on the head posture and the wrist posture, and (iii) determine whether hands have left handlebars based on the relative wrist-to-head posture and the height difference.

15. A non-transitory computer storage medium comprising program instructions that, when executed by a processor, cause the processor to perform the method according to claim 1.

16. The method as recited in claim 1, further comprising transmitting a notification signal in response to determining that a riding anomaly or fall has occurred.

* * * * *